United States Patent [19]

Bollag

[11] Patent Number: 4,719,238

[45] Date of Patent: Jan. 12, 1988

[54] TREATMENT OF DISEASES WHICH CAUSE PATHOLOGICAL CORNIFICATION OF THE EPIDERMIS OF THE SKIN

[75] Inventor: Werner Bollag, Basel, Switzerland

[73] Assignee: Hoffmann-La Roche Inc., Nutley, N.J.

[21] Appl. No.: 56,072

[22] Filed: Jun. 1, 1987

Related U.S. Application Data

[62] Division of Ser. No. 874,935, Jun. 16, 1986, Pat. No. 4,689,350.

[30] Foreign Application Priority Data

Jun. 28, 1985 [CH] Switzerland .................. 2753/85

[51] Int. Cl.$^4$ ........................................... A61K 31/015
[52] U.S. Cl. .................................................. 514/765
[58] Field of Search ........................................ 514/765

[56] References Cited

U.S. PATENT DOCUMENTS 4,326,055  8/1982  Loeligen ..................... 514/863
4,588,750  5/1986  Boris ........................... 514/852

*Primary Examiner*—Stanley J. Friedman
*Attorney, Agent, or Firm*—Jon S. Saxe; George M. Gould; William H. Epstein

[57] ABSTRACT

1,2,3,4-Tetrahydro-1,1,4,4-tetramethyl-6-(alpha-methylstyryl)naphthalene possesses antikeratinizing, antiinflammatory and immunomodulatory properties and can be used in the treatment or prevention of dermatoses which are accompanied by a pathological cornification as well as inflammatory, autoimmune, rheumatic and allergic illnesses.

10 Claims, No Drawings

TREATMENT OF DISEASES WHICH CAUSE PATHOLOGICAL CORNIFICATION OF THE EPIDERMIS OF THE SKIN

This is a division of application Ser. No. 874,935 filed June 16, 1986, now U.S. Pat. No. 4,689,350.

BACKGROUND OF INVENTION

This invention is directed to the treatment of certain dermatoses as well as inflammation associated with various diseases. It has been known to utilize the compound 1,2,3,4-tetrahydro-1,1,4,4-tetramethyl-6-(alpha-methylstyryl)-naphthalene which has the formula

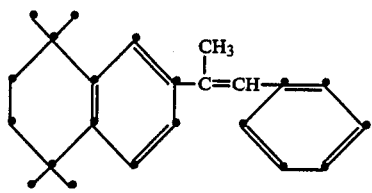

I for the systemic and topical treatment or prevention of conditions caused by an increased sebum secretion, such as greasy hair, oily scalp, seborrhea and especially acne vulgaris. See U.S. Pat. No. 4,588,750, Boris, issued May 13, 1986. Prior to its discovery for use in the treatment or prevention of conditions caused by increased sebum secretion, the compound of formula I had been found biologically inactive in preliminary screening tests, see Rydell et al., Acta pharmacol. et toxicol., 51, 413–420 (1982); Kistler, Calcif Tissue Int. 33, 249–254 (1981) and Loeliger et al., Eur. J. Med. Chem.-Chimica Therapeutica, 15, No 1, 9–15 (1980).

While retinoids other than the compound of formula I including those disclosed in U.S. Pat. No. 4,326,055, Loeliger, Apr. 20, 1982, have been found active to reduce sebum secretion, and treat certain dermatoses as well as inflammation, these retinoids produce deleterious side effects such as hypervitaminosis A. Therefore, it has long been desired to provide a compound which can be used to treat inflammatory illnesses and dermatoses in a clinical setting.

SUMMARY OF INVENTION

In accordance with this invention, it has been found that the compound of formula I above can be used for treating inflammation associated with inflammation producing diseases as well as treating diseases which cause pathological cornification of the epidermis of the skin by administering the compound of formula I above in an amount sufficient for effecting said treatment. Furthermore the compound of formula I can be administered either systemically or topically for treating said diseases and disorders, without producing side effects such as hypervitaminosis A, skin irritations and teratogenicity generally associated with retinoids.

DETAILED DESCRIPTION

In the scope of the present invention it has been found that 1,2,3,4-tetrahydro-1,1,4,4-tetramethyl-6-(alpha-methylstyryl)naphthalene of the formula I possesses antikeratinizing, antiinflammatory and immunomodulatory properties. It has now surprisingly been found that aforementioned pathological conditions can be effectively treated by administering the compound of formula I systemically and topically. The present invention is based on the aforementioned finding and is accordingly concerned with the novel use of the compound of formula I in the treatment or prevention of dermatoses which are accompanied by a pathological cornification as well as treating the inflammation caused by inflammatory, autoimmune, rheumatic and allergic illnesses.

In accordance with this invention, it has been found that the compound of formula I is effective in treating the inflammation associated with inflammatory producing diseases. By administration of the compound of formula I to patients suffering from these diseases, the inflammation is treated by inhibiting or decreasing the progress of the inflammation produced by these diseases. Among the inflammatory producing diseases which can be treated in accordance with the method of this invention are diseases of a rheumatic, inflammatory, allergic or autoimmune nature.

Among the inflammatory producing diseases which can be treated in accordance with this invention are included inflammatory and rheumatic illnesses such as acute and chronic inflammations of the skin and mucous membranes, primary-chronic polyarthritis (rheumatoid arthritis), spondylarthritis ankylopoetica, osteoarthritides, arthritides and arthroses of the widest diversity of joints and of an inflammatory and degenerative nature; allergic illnesses of skin and mucous membranes such as eczemas of acute, subacute and chronic nature, allergic rhinitis, bronchitis with and without asthmatic components, atopic dermatitis; and autoimmune illnesses, e.g. lupus erythematosus and Reiter's syndrome.

In accordance with this invention, it has been found that the compound of formula I above can be used in treating abnormal cornification of the epidermis of the skin produced by various dermatological diseases as a result of abnormal differentiation of the cells within the skin. Through abnormal differentiation, the skin does not grow correctly causing scaling, uneven thickening, and lesions within the epidermis of the skin. The administration of an effective amount of the compound of formula I to a patient suffering from these diseases decreases the amount of abnormal cornification of the skin and corrects the abnormality in differentiation of the skin cells. Through the use of the compound of formula I above, the amount of scaling and uneven thickness produced by diseases which cause abnormal cornification of the epidermis of the skin is reduced.

The diseases which cause abnormal cornification of the skin include all forms of psoriasis, e.g. psoriasis vulgaris, psoriasis pustulosa, psoriasis erythrodermica, psoriasis arthropathica, parapsoriasis, palmoplantar pustulosis, all forms of ichthyoses, e.g. ichthyosis vulgaris and congenital ichthyoses, keratodermias of all types, e.g. palmoplantar keratodermia, other genodermatoses with pathological cornification disorders, e.g. Darier's disease, further lichen ruber planus and pityriasis rubra pilaris.

The (E)-isomer of the compound of formula I, i.e. 1,2,3,4-tetrahydro-1,1,4,4-tetramethyl-6-[(E)-alpha-methylstyryl]naphthalene (compound Ia), is preferred for the uses in accordance with the invention, although the (Z)-isomer, i.e. 1,2,3,4-tetrahydro-1,1,4,4-tetramethyl-6-[(Z)-alpha-methylstyryl]naphthalene (compound Ib), can likewise be used in the scope of the present invention, alone or in combination with the preferred (E)-isomer.

For the treatment or prevention of the illnesses mentioned above the compound of formula I is administered systemically or topically, preferably systemically, especially enterally and particularly orally.

The dosage in the case of systemic administration and preferably oral administration varies in accordance with the requirements of the individual patient as determined by the treating physician. In general, however, a daily dosage of about 1 mg to about 50 mg per kg body weight, preferably of about 3 mg to about 15 mg, per kg body weight of the patient should be used. The dosage can be administered as a single dosage or in several divided dosages apportioned in accordance with a dosage plan as determined by the physician in accordance with the requirements of the patient.

As administration forms for systemic administration there come into consideration usual solid or liquid dosage forms, e.g. suppositories or as solid oral dosage forms capsules, tablets, dragees, pills, powders, granulates and the like, as liquid oral dosage forms solutions, syrups, suspension, elixirs and the like and as parenteral dosage forms infusion or injection solutions which can be injected intravenously or intramuscularly.

It is possible in the scope of the present invention to incorporate the compound of formula I in the enteral or parenteral dosage form in any amount which is suitable for systemic administration. It is, however, preferred to manufacture preparations which contain the active substance in accordance with the invention in an amount of about 50–1000 mg, preferably of about 150–500 mg. The manufacture of capsules and tablets is especially preferred.

Solutions, lotions, suspensions, salves, creams, gels, micronized powders, aerosols and the like are suitable for topical administration. These preparations conveniently contain 0.1–10 wt.%, preferably 0.5–5 wt.%, of the compound of formula I calculated on the total weight of the preparation.

The manufacture of the above-mentioned systemic and topical forms of use can be carried out in the usual manner, e.g. on the basis of the Examples hereinafter.

EXAMPLE 1

Hard gelatine capsules containing the following ingredients can be manufactured:

| Ingredients | mg/capsule |
|---|---|
| 3. Spray-dried powder containing 75% of compound Ia | 200 |
| 2. Sodium dioctyl sulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

Procedure

The spray-dried powder, which is based on the active substance, gelatine and microcrystalline cellulose and which has an average particle size of the active substance of less than 1 m (measured by means of autocorrelation spectroscopy), is moistened with an aqueous solution of sodium carboxymethylcellulose and sodium dioctyl sulphosuccinate and kneaded. The resulting mass is granulated, dried and sieved, and the granulate obtained is mixed with microcrystalline cellulose, talc and magnesium stearate. The powder is filled into size 0 capsules.

EXAMPLE 2

Tablets containing the following ingredients can be manufactured:

| Ingredients | mg/tablet |
|---|---|
| 3. Compound Ia as a finely milled powder | 500 |
| 2. Lactose powd. | 100 |
| 3. Maize starch white | 60 |
| 4. Povidone K30 | 8 |
| 5. Maize starch white | 112 |
| 6. Talc | 16 |
| 7. Magnesium stearate | 4 |
| Total | 800 |

Procedure

The finely milled substance is mixed with powd. lactose and white maize starch. The mixture is moistened with an aqueous solution of Povidone K30 and kneaded and the resulting mass is granulated, dried and sieved. The granulate is mixed with white maize starch (2nd portion), talc and magnesium stearate and pressed to tablets of suitable size.

EXAMPLE 3

Soft gelatine capsules containing the following ingredients can be manufactured:

| Ingredients | mg/capsule |
|---|---|
| 1. Compound Ia | 50 |
| 2. Triglyceride | 450 |
| Total | 500 |

Procedure 10 g of compound Ia are dissolved in 90 g of medium-chain triglyceride with stirring, inert gasification and protection from light. This solution is processed as the capsule fill mass by a contract manufacturer to soft gelatine capsules containing 50 mg of active substance.

EXAMPLE 4

A fatty salve containing the following ingredients can be manufactured:

| Ingredients: | |
|---|---|
| 1. Compound Ia, finely milled | 3.0 g |
| 2. Paraffin oil, internally viscous | 30.0 g |
| 3. Lunacera M | 15.0 g |
| 4. Castor oil, hardened | 5.0 g |
| 5. Vaseline, white ad | 100 g |

Procedure

All adjuvants are mixed in the warm and stirred while cooling to room temperature. The active substance is homogeneously mixed with the mixture obtained in this manner in the cold under protection from light.

EXAMPLE 5

A fatty cream containing the following ingredients can be manufactured:

| Ingredients | | |
| --- | --- | --- |
| 1. Compound Ia, finely milled | 3.0 g | |
| 2. Vaseline, white | 30.0 g | |
| 3. Wax, white | 5.0 g | fatty phase |
| 4. Paraffin oil, internally viscous | 20.0 g | |
| 5. Dehymuls E | 9.0 g | |
| 6. Benzoic acid | 0.2 g | aqueous phase |
| 7. Demineralized water ad | 100.0 g | |

Procedure

Fatty phase and aqueous phase are processed to a fatty cream. The active substance is homogeneously mixed with this fatty cream at room temperature under protection from light.

EXAMPLE 6

A vanishing cream (o/w emulsion type) containing the following ingredients can be manufactured:

| Ingredients: | | |
| --- | --- | --- |
| 1. Compound Ia, finely milled | 3.0 g | |
| 2. Glycerine monostearate | 17.0 g | |
| 3. Deltyl extra | 4.0 g | |
| 4. Tween 60 | 4.0 g | fatty phase |
| 5. Span 60 | 4.0 g | |
| 6. Silicon oil AR 20 | 2.0 g | |
| 7. Propylene glycol | 10.0 g | |
| 8. Benzoic acid, pure | 0.2 g | aqueous phase |
| 9. Demineralized water ad | 100.0 g | |

Procedure

The fatty phase and aqueous phase are processed to a cream. The active substance is homogeneously mixed with this cream at room temperature under protection from light.

EXAMPLE 7

A hydrophilic gel containing the following ingredients can be manufactured:

| Ingredients: | |
| --- | --- |
| 1. Compound Ia, finely milled | 3.0 g |
| 2. Carbopol 940 | 2.5 g |
| 3. Propylene glycol | 50.0 g |
| 4. Ethanol, 94% ad | 100.0 g |

Procedure

The active substance is incorporated in the polypropylene glycol/ethanol (94%) mixture under protection from light. Carbopol 940 is stirred in until gelling is complete.

EXAMPLE 8

A lotion containing the following ingredients can be manufactured:

| Ingredients: | |
| --- | --- |
| 1. Compound Ia, finely milled | 3.0 g |
| 2. Carbopol 934 | 0.6 g |
| 3. Sodium hydroxide | q.s. ad pH 6 |
| 4. Ethanol, 94% | 50.0 g |
| 5. Demineralized water ad | 100.0 g |

Procedure

The active substance is incorporated into the ethanol (94%)/water mixture under protection from light. Carbopol 934 is stirred in until gelling is complete and the pH value is adjusted with sodium hydroxide.

The therapeutic and prophylatic activity of the compound of formula I in dermatoses which are accompanied by a pathological cornification as well as of inflammatory, rheumatic and allergic illnesses can be concluded from the following experiments:

(A) The antikeratinizing activity of compound Ia was determined on the Rhino mouse model according to the following procedure. The skin of the Rhino mouse is characterized by the presence of keratin-filled utriculi of the epidermis and subcutaneous cysts, both of which are derived from hair follicles. The administration of retinoids leads to a hyperproliferation of the epidermis and of the wall epithelium of the utriculi. The acanthosis of the epidermis and the reduction in the size of the utriculi lead to a normalization of the altered structure of the epithelial layer. The daily topical application of 0.1 ml/cm$^2$ skin of the Rhino mouse of a 3% acetone solution of compound Ia over a period of 3 weeks or the thrice weekly oral administration of compound Ia in arachis oil over a period of 3 weeks leads to a significant proliferation of the epidermis and a striking reduction of the keratin-filled utriculi. The results are compiled in Tables I and II.

TABLE I

| Topical use of compound Ia over a period of 3 weeks | | | |
| --- | --- | --- | --- |
| | Keratin-filled utriculi | | |
| Treatment Daily topical use of 0.1 ml/cm$^2$ | $\phi$ D1 of the utriculus in $\mu$m measured at the widest point | $\phi$ D2 of the utriculus in $\mu$m (measured at the orifice) | $\frac{D1}{D2}$ |
| Acetone | 154.0 | 74.4 | 2.2 |
| Compound Ia 3% in acetone | 76.9 | 59.7 | 1.3 |

TABLE II

| Systemic use of compound Ia over a period of 3 weeks | | | |
| --- | --- | --- | --- |
| | Keratin-filled utriculi | | |
| Treatment 3× weekly orally | $\phi$ D1 of the utriculus in $\mu$m (measured at the widest point) | $\phi$ D2 of the utriculus in $\mu$m (measured at the orifice) | $\frac{D1}{D2}$ |
| Arachis oil | 135.1 | 71.5 | 1.9 |
| Compound Ia | | | |
| 25 mg/kg | 116.8 | 72.4 | 1.6 |
| 75 mg/kg | 90.2 | 62.2 | 1.4 |
| 225 mg/kg | 88.7 | 67.2 | 1.3 |

(B) The antiallergic activity of compound Ia was determined on mice according to the following method. Groups of 10 male mice of a minimum weight of 20 g were sensitized on day 0 with methylated bovine serum albumin (MBSA). The sensitization was effected at two positions on the shaved abdominal flanks by the intradermal injection of in each case 0.05 ml of a 1:1 mixture (v/v) of 0.5% MBSA and Freund's complete adjuvant. 9 days later (day 8) 0.02 ml of 1% MBSA was injected subplantarly into one hind paw as a "challenge" to the experimental animals, while the same volume of a sterile sodium chloride solution was injected into the other hind paw. 24 hours later (day 9) the inflammation was estimated on the basis of the oedema caused by the injection. The volumes of the paws were measured by water displacement plethysmography. The test compound Ia was administered orally to the experimental animals on days 0 to 4, i.e. over a period of 5 days, and the results of the animals treated with compound Ia were compared with those of the control animals treated only with the vehicle. The results were calculated as follows: for each mouse the percentage increase in the paw volume after the "challenge" administration of the MBSA was calculated according to the formula $$\frac{\text{"Challenge" paw volume minus control paw volume}}{\text{Control paw volume}} \times 100\%$$

Thereafter, the average increase in the paw volume was calculated for each group and the percentage decrease in the paw volume of the animals treated with compound Ia compared with the control animals was calculated as follows:

$$\frac{\%\text{ Increase in the paw volume of the control animals minus}}{\%\text{ Increase in the paw volume of the control animals}} \times 100\%$$

The results are compiled in Table III.

TABLE III

| Compound Ia mg/kg/mouse/day, p.o. | % Reduction in the paw volume compared with controls |
|---|---|
| 30 | 9 |
| 100 | 38 |

(C) The anti-inflammatory and anti-rheumatic activity of compound Ia was, furthermore, determined on rats according to the following method. Adjuvant arthritis was produced in each of 5 female rats weighing 115–170 g according to the method of Newbould. Thus, in each case 0.1 ml of adjuvant consisting of a homogenized suspension of heat-killed Mycobacterium tuberculosis (human strains C, DT and PN), 5 mg/ml, in liquid paraffin was injected subplantarly into the right hind paw of the rats. From the day of the adjuvant injection up to the end of the experiment on the 15th day the test compound Ia was administered orally each day in dosages of 15, 45, 100 and 200 mg/kg in arachis oil. The primary swelling of the paw injected with the adjuvant was determined in each case by means of water displacement plethysmography on days 3 and 7. The secondary swelling of the paw injected with the adjuvant and of the non-injected paw was determined at the end of the experiment on day 15 likewise by means of water displacement plethysmography. The percentage change in the paw volume was calculated by comparison with the controls. In addition, further parameters of the secondary reaction were given, namely the flexibility of the ankle joint of the non-injected paw as well as a recordal of the total lesions by degree. The flexibility of the joint is measured by the degree of rotation between the maximum stretching and bending of the non-injected paw of each rat. The average for each group, inclusive of that of the control animals, is calculated and the result is given as the percentage improvement of the control value. In order to determine the total lesions noses, ears, front paws, non-injected hind paw and tail are examined and the lesions are determined on a scale with values between 0 and 3. The average value for each group is calculated and the results are given as a percentage change compared with the controls. The results are compiled in Table IV.

TABLE IV

| Compound Ia mg/kg/rat/day, p.o. | Change in the paw volume in % compared with controls | | | | Change in the | |
|---|---|---|---|---|---|---|
| | Injected paw | | | Non-injected Paw | joint mobility % | total lesions % |
| | Swelling day 3 | Swelling day 7 | Swelling day 15 | Swelling day 15 | | |
| 15 | −6.3 | −1.3 | −8.0 | −37.8 | +16.7 | −38.7 |
| 45 | +6.3 | +1.2 | −9.5 | −39.9 | +13.3 | −37.6 |
| 100 | −4.9 | +4.7 | −14.8 | −77.7 | +57.7 | −80.7 |
| 200 | −18.2 | −0.3 | −17.0 | −91.6 | +76.9 | −100.0 |

It is known that 1,2,3,4-tetrahydro-1,1,4,4-tetramethyl-6-[(E)-alpha-methylstyryl]naphthalene Ia is well tolerated and that no toxic symptoms appear in the therapeutically indicated dosages. Thus, compound Ia does not exhibit, in particular, any hypervitaminosis A phenomena (e.g. no manifestations on skin and mucous membranes) and is non-teratogenic and not irritating to the skin. Over and above this it has been shown that compound Ia, as a sole therapeutically active retinoid, brings about no increase in the lipid value in blood plasma, but on the contrary even possesses a lipid-lowering activity.

In order to detect this activity a dosage of compound Ia was administered five times per dosage to 5 male and 5 female albino rats (Fullinsdorf/Switzerland) weighing approximately 150 g by means of a probang within 2 days in intervals of in each case 18 and 6 hours. 18 hours after the last application 1–1,2 ml of blood plasma were removed retroorbitally from the experimental animals. The triglyceride value was determined by enzymatic cleavage of the triglyceride with subsequent determination of the resulting glycerine (colour reaction) by means of Peridochrom triglyceride GPO-PAP. The results are compiled in Table V.

TABLE V

| | Male rats | Female rats |
|---|---|---|
| Control animals Compound of formula Ia | 201 ± 39 mg/100 ml | 69 ± 28 mg/100 ml |
| 10 mg/kg | 158 ± 56 mg/100 ml | 56 ± 25 mg/100 ml |
| 100 mg/kg | 173 ± 18 mg/100 ml | 72 ± 18 mg/100 ml |
| 1000 mg/kg | 41 ± 19 mg/100 ml | 30 ± 8 mg/100 ml |

The clinical effectiveness of compound Ia is illustrated by the following examples:

7 patients with psoriasis vulgaris and 1 patient with psoriasis pustulosa were treated over a period of 12–16 weeks with a daily oral dosage between 96 and 300 mg of compound Ia. The psoriatic lesions (erythema, infiltration, scaling, pustules) which existed at the beginning of the treatment diminished in the course of the treatment in intensity and dimension by 30–60%. Apart from the objectively determinable remissions, the subjective symptoms of the patients were also clearly improved. In contrast to all retinoids hitherto used clinically, compound Ia caused no symptoms of a hypervitaminosis A and also no other side effects. Thus, in particular, no objective or subjective symptoms on the skin, hair, mucous membranes, bones, joints, muscles or nervous system were ascertained. All laboratory values (haematology, blood chemistry, urine analysis) remained in the range of the starting values in the course of the treatment. In particular, the determination of transaminases, alkaline phosphatase, cholesterol and triglycerides showed no abnormal changes.

1 patient with chronic eczema on all parts of the body and who had had every 2–4 weeks for 3 years a massive eruption of the illness showed under the daily treatment with 192 mg of compound Ia orally over a period of 3 months a very good effect, whereby generally eruptions no longer occurred. The patient showed no side effects.

I claim:

1. A process for the treatment of diseases which cause pathological cornification of the epidermis of the skin comprising administering to patients suffering from said diseases, the compound 1,2,3,4-tetrahydro-1,1,4,4-tetramethyl-6-(alpha-methylstyryl)napthalene, said compound being administered in an amount effective to treat the disease.

2. The process of claim 1 wherein said disease is psoriasis or ichthyoses.

3. The process of claim 2 wherein said compound is administered orally.

4. The process of claim 3 wherein said compound is administered to said patient at a daily dose of from 1 mg/kg of body weight to about 50 mg/kg of body weight.

5. The process of claim 4 wherein said compound is administered at a dose of from 3 mg/kg to 15 mg/kg.

6. The process of claim 5 wherein said compound is administered in a unit dosage containing from about 150 mg to about 500 mg of said compound.

7. The process of claim 6 wherein said unit dosage is a capsule or tablet.

8. The process of claim 2 wherein said compound is administered topically.

9. The process of claim 8 wherein said compound is administered in a topical preparation containing from about 0.1% to about 10% by weight of said compound.

10. The process of claim 9 wherein said topical preparation is a gel, cream, solution, lotion or suspension.

* * * * *